United States Patent
Turner

(10) Patent No.: US 11,241,523 B2
(45) Date of Patent: Feb. 8, 2022

(54) FLOW CONTROL SYSTEM

(71) Applicant: SPECTRUM MEDICAL LTD., Gloucester (GB)

(72) Inventor: Stephen Turner, Gloucestershire (GB)

(73) Assignee: SPECTRUM MEDICAL LTD.

( * ) Notice: Subject to any disclaimer, the term of this patent is extended or adjusted under 35 U.S.C. 154(b) by 422 days.

(21) Appl. No.: 16/472,194

(22) PCT Filed: Dec. 19, 2017

(86) PCT No.: PCT/GB2017/053814
§ 371 (c)(1),
(2) Date: Jun. 20, 2019

(87) PCT Pub. No.: WO2018/115851
PCT Pub. Date: Jun. 28, 2018

(65) Prior Publication Data
US 2020/0086034 A1 Mar. 19, 2020

(30) Foreign Application Priority Data
Dec. 23, 2016 (GB) ...................................... 1622108

(51) Int. Cl.
*A61M 1/36* (2006.01)
*A61M 60/00* (2021.01)

(52) U.S. Cl.
CPC ........ *A61M 1/3624* (2013.01); *A61M 1/3627* (2013.01); *A61M 1/3666* (2013.01); *A61M 60/00* (2021.01); *A61M 2205/3334* (2013.01)

(58) Field of Classification Search
CPC .............. A61M 1/3621; A61M 1/3624; A61M 1/3627; A61M 1/3666; A61M 2205/3336; A61M 60/00
See application file for complete search history.

(56) References Cited

U.S. PATENT DOCUMENTS 5,186,431 A * 2/1993 Tamari ...................... F16K 7/07
251/5
2012/0130299 A1* 5/2012 Knott .................. A61M 1/3667
604/6.15

FOREIGN PATENT DOCUMENTS

GB 2538577 A 11/2016
WO 199624397 8/1996
(Continued)

OTHER PUBLICATIONS

International Searching Authority, International Search Report and Written Opinion for application PCT/GB2017/053814, dated Mar. 12, 2018.
(Continued)

*Primary Examiner* — Philip R Wiest
(74) *Attorney, Agent, or Firm* — Quarles & Brady LLP

(57) ABSTRACT

A control system is provided to restrict the flow rate of blood in a venous line 12 of a perfusion system 1 comprising a reservoir 10 supplied by the venous line 12 and supplying an outgoing line 22. The control system comprises an outgoing flow sensor 32 configured to determine an outgoing flow value indicative of the outgoing flow rate in the outgoing line 22, and a controller configured to process the outgoing flow value and to determine if the outgoing flow value exceeds a pre-set pairing threshold. The system further comprises an adjustable restriction 28 for restricting the flow rate in the venous line 12 to maintain a venous flow rate that does not exceed a venous restriction threshold, wherein the adjustable restriction 28 is responsive to the controller and wherein the controller comprises a configuration allowing the controller to set the adjustable restriction at the level of the outgoing flow rate, to change the venous restriction threshold with the outgoing flow rate, if the outgoing flow value is above the pre-set pairing threshold.

21 Claims, 2 Drawing Sheets

(56) References Cited

FOREIGN PATENT DOCUMENTS

WO          2016027866 A1    2/2016
WO    WO-2016027866 A1 *   2/2016   .......... A61M 1/3607

OTHER PUBLICATIONS

Intellectual Property Office of the United Kingdom, Search Report for application GB1622108.7, dated May 4, 2017.

* cited by examiner

FLOW CONTROL SYSTEM

CROSS REFERENCE TO RELATED APPLICATIONS

This application represents the U.S. national stage entry of PCT/GB2017/053814 filed Dec. 19, 2017, which claims benefit of United Kingdom application 1622108.7 filed Dec. 23, 2016. The contents of these applications are hereby incorporated by reference as set forth in their entirety herein.

FIELD OF THE INVENTION

The present invention relates to a blood flow control mechanism in an extracorporeal perfusion system. In particular, the present invention relates to a control system allowing the blood flow rate in a venous line of a perfusion system to be controlled relative to the blood flow rate of an outgoing, arterial line of the perfusion system.

BACKGROUND

Extracorporeal perfusion is a process in which blood from a patient is circulated outside the patient's body and typically re-oxygenated to be returned to the patient. More specifically, venous (oxygen-reduced) blood which has been removed from a patient via a venous line is oxygenated by exposure to an oxygenation gas in an oxygenator for supply via an outgoing line, or arterial line, returning to the patient as arterial blood.

Extracorporeal perfusion is used to substitute heart and lung functionality during a medical procedure, eg open heart surgery or lung treatment. During the procedure, blood is circulated extracorporeally at a rate of typically 5 litres per minute (lpm). The early phases of perfusion are challenging because, as perfusion is initiated, the amount of blood removed from the body for extracorporeal circulation needs to undergo certain treatments for which thorough mixing with blood is desirable (eg priming constituents), while blood needs to be available for return to the patient quickly. Furthermore, initial amounts of blood available for extracorporeal circulation may be below safety margins that would be set during full operation.

The present invention is concerned with improving the options for blood supply management in the early stages of extracorporeal perfusion.

SUMMARY OF THE INVENTION

In accordance with a first aspect of the present invention, there is provided a control system to restrict the flow rate of blood in a blood line as defined in claim 1.

The control system is provided to restrict the flow rate of blood in a venous line of a perfusion system comprising a reservoir supplied by the venous line and supplying an outgoing line. The control system comprises an outgoing flow sensor configured to determine an outgoing flow value indicative of the outgoing flow rate in the outgoing line, and a controller configured to process the outgoing flow value and to determine if the outgoing flow value exceeds a pre-set pairing threshold. The system further comprises an adjustable restriction for restricting the flow rate in the venous line to maintain a venous flow rate that does not exceed a venous restriction threshold, wherein the adjustable restriction is responsive to the controller and wherein the controller comprises a configuration allowing the controller to set the adjustable restriction at the level of the outgoing flow rate, to change the venous restriction threshold with the outgoing flow rate, if the outgoing flow value is above the pre-set pairing threshold.

The outgoing line is understood to be normally the main line of a perfusion system, ie the arterial line supplying blood conditioned (eg, oxygenated, and set to a flow rate, pressure and temperature) for supply toward a patient.

The venous line is understood to be an incoming line, ie a line receiving blood for extracorporeal processing from a patient.

The adjustable restriction is understood to be a mechanism capable of limiting the flow rate in the venous line to a restriction threshold. Eg, a restriction threshold of 2 lpm would prevent blood from flowing through the venous line at a rate higher than 2 lpm.

The configuration allowing the controller to set the adjustable restriction at the level of the outgoing flow rate provides a "pairing" functionality, or "pairing mode". The pairing functionality allows the venous flow rate to be paired with the outgoing flow rate.

It is understood that the outgoing flow rate is determined by a pump mechanism of the extracorporeal perfusion system. The pump mechanism effects a flow through the outgoing line. The pump mechanism may comprise a roller pump or a centrifugal pump. The outgoing flow rate may be increased by issuing commands to a pump to increase its performance, and decreased correspondingly by decreasing pump performance. The venous flow rate may be influenced by the relative pressures.

Some degree of control over relative pressures is possible by posture and position of a patient relative to an extracorporeal reservoir, or by using a vacuum-induced pressure gradient, in order to promote drainage of venous blood into the extracorporeal reservoir. A restriction in the venous line allows the venous flow rate to be limited to a specific maximum level. The venous flow rate will be in principle "maintained" at the level set by the restriction threshold, and it is understood that, depending on circumstances, the venous flow rate may temporarily decrease below the venous restriction threshold, but will be prevented from exceeding the venous restriction threshold.

A pairing functionality facilitates the early stages of the initiation of extracorporeal perfusion. The initiation phase may be distinguished from the subsequent, established phase in that, during the initiation of perfusion, the emphasis is on slowly establishing and ensuring the extracorporeal circulation of blood such that this can be maintained during the main surgical procedure at the required flow rates in the region of 5 lpm. The initiation is concluded when a reliable blood circulation is established and maintaining blood circulation becomes secondary to other clinical requirements, e.g. such that flow rates can be modulated to maintain oxygenation levels.

The following paragraphs set out a clinical scenario in which the pairing functionality of the invention may be used. The initiation of a cardiopulmonary bypass procedure is accomplished on the command of a surgeon after adequate preparation such as, eg, the provision of anticoagulants (so-called "heparinization" of the blood). A cardiopulmonary bypass circuit commonly consists of a venous line for oxygen-reduced blood from a patient into a reservoir, an outgoing (arterial) line for oxygen-enriched blood for return to a patient, a main pump to control the flow of blood from the reservoir through the outgoing line, and various components for conditioning the blood so that it is in a condition for subsequent administration to the patient, including an oxygenator and a heat exchanger, level and bubble sensors, and various shunts, purges, filters, suction lines and vent lines, and other systems containing blood/fluid. The operation of the cardiopulmonary bypass is typically the responsibility of a specialist (perfusionist) under instructions of a surgeon. Before the cardiopulmonary bypass procedure starts, the venous line is clamped by a venous line clamp to prevent blood flow from the patient. For initiation of the cardiopulmonary bypass procedure, the perfusionist either gradually or instantly opens the venous line clamp, which allows blood to be drained from the patient into the reservoir. Venous blood flow may be assisted by application of a regulated vacuum to the venous reservoir. When it is estimated that sufficient blood volume has entered the venous reservoir, the perfusionist initiates outgoing pump flow to attempt to reach a certain balance of outgoing flow rate to venous flow rate, without exceeding the rate of venous blood return into the reservoir.

During the initial phase, venous blood return may be insufficient to allow sufficient flow out of the reservoir through the outgoing line and the various components of the system. In that case, the fluid level in the reservoir may be low. A low reservoir level is dangerous because pumping out of the reservoir faster than venous flow coming in can entrain air into the system, which can harm the patient. However, ensuring that outgoing flow is not too high is a requirement in conflict with providing outgoing blood to a patient quickly enough. When blood is not returned to the patient quickly enough, the lack of blood in the patient's arterial side of the vascular system commonly results in stress responses, in particular hypotension-induced responses. Hypotension of the vascular system can cause a stimulation of compensatory physiological mechanisms, disturbing the relative homeostasis of the patient. A similar disturbance of homeostasis is also induced when the initiation of bypass is done too quickly, because this can result in diluting the arterial vasculature with low-viscosity, poor oxygen-content priming solution (eg crystalloid fluid). The compensatory mechanisms are disturbing to the delicate balance of the vascular system, and can affect the vascular tone, viscosity, hormone balance, vascular pressure, and oxygen delivery to the tissues.

The pairing functionality of the present invention facilitates a controlled initiation of cardiopulmonary bypass. The pairing functionality is intended after an initial phase in which venous flow is permitted (by setting the venous restriction threshold to a low maximum flow rate) to fill the reservoir. In practice, the cardiopulmonary bypass procedure may be initiated by slowly draining blood via the venous line at a rate of eg, 1 lpm, which may be a safe flow rate for an adult patient, or less for a smaller patient. The initial amounts of blood in the reservoir are unlikely to suffice for a continuous supply of outgoing (arterial) blood even at low flow rates. The blood in the reservoir is usually mixed with priming solution and there is no outgoing flow (the outgoing flow rate is zero). Once the reservoir contains sufficient blood (mixed with priming solution) for a continuous supply of outgoing blood returning to the patient at low flow rates, outgoing flow is started.

While the outgoing flow is slowly increased, at levels that remain below the originally set venous restriction threshold, the advantages of the pairing functionality are not as pronounced. In this regard, by "pairing threshold", an outgoing flow rate level is meant at which, if exceeded, the pairing functionality is activated such that the venous restriction threshold is set to match the level of the outgoing flow rate. This allows the pairing mode to be activated automatically, thereby reducing the requirement for a clinician to direct attention to the activation of the pairing mode.

The pre-set pairing threshold may be at the same level as the initially set venous restriction threshold. Eg, the system may comprise a configuration whereby the manual selection of an initial venous restriction threshold (eg, 1 lpm) also sets the pairing threshold to the venous restriction threshold (ie, 1 lpm).

Once the amount of blood in the reservoir exceeds a safety threshold, outgoing flow can be increased above the venous restriction threshold. At this stage the pairing functionality helps to ensure that the venous flow is allowed to increase as soon as this is justifiable, ie when the outgoing flow increases further. This means that a clinician can direct attention on setting appropriate outgoing flow parameters. By way of the invention, the venous restriction threshold will automatically start to adjust, and continue to adjust, to match the outgoing flow rate.

To provide an illustrative example, the pairing threshold and the venous restriction threshold may be set to 1 lpm. While the outgoing flow rate is lower than the pairing threshold of 1 lpm, venous blood is allowed to be drained at a rate of up to 1 lpm, but prevented from exceeding 1 lpm. Once a sufficient amount of blood has been collected in the reservoir (and usually mixed with priming solution), the clinician may initiate blood flow from the reservoir through the outgoing line. While the outgoing flow rate is below the pairing threshold of 1 lpm, a change in the outgoing flow rate will not affect the venous restriction threshold. When the outgoing flow rate exceeds the pairing threshold of 1 lpm, eg is increased to 2 lpm, the pairing functionality is automatically activated and the venous restriction threshold is increased accordingly to 2 lpm, meaning that venous blood is allowed to be drained at a rate of up to 2 lpm, while being prevented from exceeding 2 lpm.

A gradual bypass initiation reduces the risk of administering a higher concentration than necessary of a so-called priming solution, which is mixed with blood, and which usually results in undesired stress responses (eg, priming solution may have a different viscosity and is unable to transport oxygen to the extent blood can).

In practice, the invention facilitates the setting of low rates of outgoing (arterial) flow and venous flow. This reduces the risk of hypotension and allows cardiopulmonary perfusion to be initiated more smoothly/slowly than is practically possible in current practice.

The system may comprise a configuration in which the pairing functionality can be activated manually, via an input interface, regardless of a pre-set pairing threshold.

In some embodiments, the system further comprises a venous flow sensor configured to determine a venous flow value indicative of the venous flow rate in the venous line, wherein the controller is configured to process the venous flow value, and wherein the adjustable restriction is responsive to the controller to reduce the venous flow rate in the venous line to maintain a venous flow rate that does not exceed the venous restriction threshold.

A venous flow sensor in combination with a responsive adjustable restriction provides a closed loop control, ensuring an upper limit of the venous drainage rate is maintained regardless of temporary fluctuations in the venous flow rate. This further improves the safety of the system, because this reduces, and practically eliminates, the risk of the venous flow rate not actually corresponding to the outgoing flow rate.

As such, the configuration combines two control loops, one control loop to ensure the venous restriction threshold is raised synchronously with the outgoing flow rate, and one control loop to ensure the actual venous flow rate is maintained by measuring the actual venous flow rate and continually readjusting the venous restriction threshold at the actual level set in accordance with the outgoing flow rate.

In some embodiments, the controller is configured to set the venous restriction threshold independently of the outgoing flow rate if the outgoing flow rate is below the pairing threshold.

If the outgoing flow rate is lower than the pairing threshold, the venous restriction threshold may be set and readjusted independently of the outgoing flow rate. An automatic de-activation of the pairing functionality removes the requirement for a clinician to direct attention on manually de-activating the pairing mode.

In some embodiments, one or more of the flow sensors are constituted by an arrangement determining the flow rate from pump parameters of one or more pumps of the perfusion system, and/or by an arrangement determining the flow rate from control input for the one or more pumps.

For instance, the main pump of the outgoing line may be calibrated and a pump stroke/rpm value may be related to a flow rate. The outgoing flow value entered via an input device may be used to both send control signals to the pump and to set the venous restriction threshold.

In some embodiments, the control system comprises a reservoir level sensor to determine a reservoir level of fluid in the reservoir, and the controller is configured to modulate the outgoing flow rate to prevent the outgoing flow rate from exceeding the venous flow rate if the reservoir level is below a reservoir level safety threshold, so as to arrest a decrease of fluid in the reservoir.

In some embodiments, the system comprises a reservoir level sensor to determine a reservoir level of fluid in the reservoir, and the controller is configured to maintain a venous flow rate that does not exceed the level of the outgoing flow rate if the reservoir level is above a reservoir level safety threshold.

Throughout the bypass procedure and its initiation, clinicians need to be able to ensure a minimum level of blood in the reservoir. United Kingdom patent application GB1516331.4 by the present applicant, published as GB2538577A, the contents of which are incorporated by reference, discloses a reservoir level control system to prevent the outgoing flow rate from exceeding the venous flow rate, in order to arrest a decrease of blood in the reservoir. The present arrangement comprises a reservoir level control that may be activated if the amount of blood in the reservoir is below a safe level.

During low flow rates, a lower fluid level in the reservoir and therefore a smaller safety margin may be acceptable, because lower flow rates provide clinical staff with more response time. The reservoir level safety threshold is set in line with these considerations.

The following paragraphs provide an illustration of the interplay between the functionalities. Venous draining may be initiated with a venous restriction threshold of 1 lpm and with a pairing threshold of 1 lpm. When the outgoing flow rate exceeds 1 lpm, eg is set to a setpoint of 2 lpm, the pairing functionality is automatically activated as the outgoing flow rate exceeds the pairing threshold. This causes the venous restriction threshold to be matched and to be set automatically to 2 lpm. While outgoing flow and venous flow are matched, the reservoir level would not normally be expected to decrease, but it may decrease for a variety of reasons, including a temporarily decreased venous flow, other blood losses or diversions. As outgoing blood is continued to be pumped at 2 lpm, this leads to a temporary decrease of the reservoir blood level.

If the reservoir blood level decreases below the reservoir level safety threshold, the reservoir level functionality is automatically activated and the outgoing flow rate is reduced (by modulating pump performance) to remain below the actual venous flow rate. While the outgoing flow rate is maintained lower than the venous flow rate, the reservoir level is expected to rise with an increase of the venous flow rate. The venous flow rate may return to its previous rate of 2 lpm but cannot exceed this threshold due to the venous flow restriction. Once the blood level in the reservoir exceeds the reservoir level safety threshold, the outgoing flow rate is increased to the set level of 2 lpm (by modulating pump performance).

While a reservoir level safety control is active, the control system may comprise a configuration permitting it to reduce the venous restriction synchronously with the outgoing flow rate (in line with the pairing mode). This will prevent the venous flow rate from becoming disproportionally high relative to the outgoing flow rate but may slow the replenishing of the reservoir. The control system may comprise a configuration maintaining the venous restriction threshold at the level before reservoir level control activated, so that the venous flow rate is not affected by a temporary reduction of the outgoing flow rate. This will allow the reservoir to be filled more quickly than would be the case with a more restricted venous flow.

In some embodiments, the control system is further configured to alter a threshold level or sensitivity as monitored by one or more sensors of the perfusion system in response to a change of the venous restriction threshold and/or of the outgoing flow value.

In some embodiments, the control system is configured to alter the threshold level or sensitivity synchronously with a change of the venous restriction threshold and/or the outgoing flow value.

In some embodiments, the control system is configured to alter the threshold level or sensitivity if the venous restriction threshold and/or the outgoing flow value exceeds or falls below a sensitivity threshold.

In some embodiments, the threshold level or sensitivity as monitored by one or more sensors is for one or more of a reservoir level safety threshold, a bubble value, a pressure threshold, a flow rate threshold, a blood value, or combinations thereof.

It may be acceptable to set certain safety thresholds to less strict values while the flow rates are lower and therefore allow more response time. Furthermore, in the circumstances it can be expected that the attention of the clinician is directed to the specific aspects of the bypass initiation, eg "filling the reservoir", because routine levels are not yet established, and so it may be desirable to set certain safety thresholds to less strict values. It is understood that by "less strict", a lower limit or a higher limit may be meant. For instance, the reservoir level safety threshold may be set lower than it would be set during established bypass blood flow. As another example, the bubble filter for detecting air bubbles in blood may be set to a "coarse" setting, because the viscosity of the initial blood and priming mixture may result in false positives. The conclusion of the bypass initiation phase may be indicated by an outgoing flow value of over 4.5 lpm, meaning that bypass is established. Thus, the system may be configured to set the bubble threshold automatically to a "fine" setting when the outgoing flow value exceeds a threshold of 4.5 lpm. The "fine" setting may be more sensitive.

In some embodiments, the controller comprises a processor and software instructions implemented by the processor, and the adjustable restriction comprises instructions implemented by the processor.

Aspects of the invention also encompass methods of controlling the venous flow restriction in line with the capabilities of the flow control system. According to a second aspect of the present invention there is provided a method restricting the flow rate of blood in a venous line of a perfusion system as defined in claim 12.

DESCRIPTION OF THE FIGURES

Exemplary embodiments of the invention will now be described with reference to the Figures, in which.

DESCRIPTION

Figure 1:
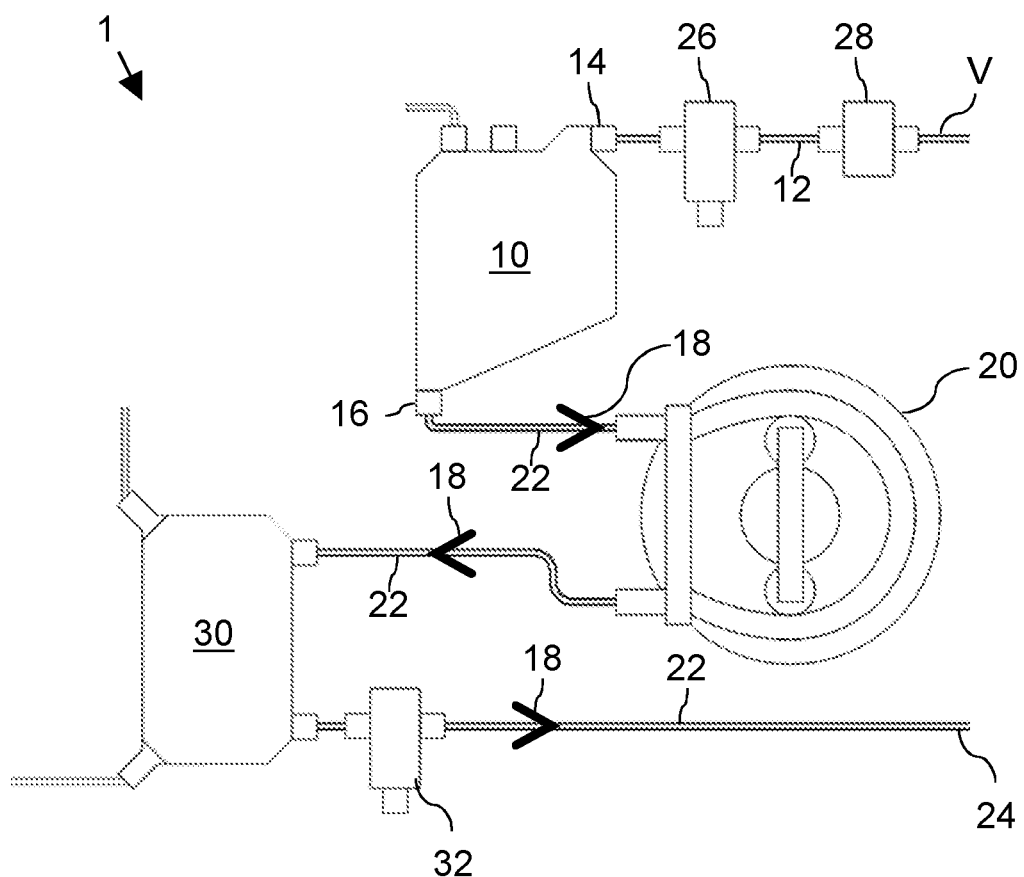
FIG. 1 shows a schematic arrangement of components of a control system to restrict the flow rate in a blood line in accordance with embodiments of the present invention.

FIG. 1 shows, schematically, components of a perfusion system 1. The perfusion system comprises a venous line 12 provided to receive venous blood V from a patient. When the venous line 12 is open, venous blood is permitted to flow into a reservoir 10 via a reservoir inlet 14. Venous blood is held in the reservoir 10 at atmospheric pressure, and held to be drawn via a reservoir outlet 16.

The reservoir 10 comprises a level sensor arrangement (not shown in FIG. 1) allowing it to determine the blood level in the reservoir. The level reservoir arrangement includes a configuration for determining whether or not the blood level in the reservoir is above or below a low blood level threshold. The low blood level threshold may be to a level below which there is an increased risk of gas being drawn through the reservoir outlet 16.

The venous blood may be drawn from the reservoir 10 via the reservoir outlet 16 through the outgoing line 22 (or main line 22) of the perfusion system. The blood is pumped by a pump 20, which may be any suitable type of pump, such as a peristaltic pump (eg, a roller pump) or a centrifugal pump. The pump causes blood to flow through the outgoing line 22 in a direction indicated by arrows 18, via an oxygenator 30 and towards an outlet 24 of the perfusion system 1.

At the outlet 24, the blood is in a condition for administration to a patient. For instance, the blood may have been oxygenated in the oxygenator 30, and the blood will have a flow rate and line pressure sufficient to permit safe administration to a patient. In the absence of losses, it can be assumed that the flow rate and the line pressure are determined by the pump 20. If the pump 20 generates higher throughput, the outgoing flow rate is faster. Conversely, if the pump 20 generates lower throughput, the outgoing flow rate is slower.

The venous line 12 and the outgoing line 22 may be constituted by flexible tubing. The tubes may have a different length and/or diameter. The tubes may have different strength or flexibility characteristics.

In the venous line 12, the control system comprises a flow-restricting arrangement 28. The flow-restricting arrangement 28 may be configured to allow the flow to be restricted gradually. For instance, the flow-restricting arrangement 28 may be constituted by a motorised clamp suitable to squeeze a flexible tube. The flow-restricting arrangement 28 constitutes an adjustable restriction.

Downstream of the reservoir 10, (in FIG. 1 also downstream of the oxygenator 30), the perfusion system is provided with an outgoing flow sensor 32. The outgoing flow sensor 32 allows the outgoing flow rate, ie the flow rate of the blood provided towards the patient to be measured. The flow rate towards the patient may be regarded as outgoing flow rate. The outgoing flow sensor 32 is configured to provide an outgoing flow value indicative of the flow rate in the outgoing line, ie, of the flow rate through the outlet 24. The outgoing flow sensor 32 may be constituted by an ultrasound flow meter or a mass flow meter. The flow sensor may be positioned at a different location of the system, or may be constituted by an arrangement determining the outgoing flow rate from operational parameters of the pump 20. The outgoing flow sensor 32 may be constituted by an arrangement determining the flow rate from a control input for the pump 20.

A controller (not shown in FIG. 1) is configured to receive as an input the outgoing flow rate and to set the restriction threshold to set a maximum flow rate through the venous line 12. In another mode of operation, the restriction threshold may be set via an interface. The restriction threshold may be set as an absolute value (eg, 2 lpm) or as a relative value (eg, 110% of the current flow).

The motorised clamp is responsive to the controller (controller not shown in FIG. 1) and allows the flow rate in the venous line to be prevented from exceeding a restriction threshold. The controller comprises decision logic permitting it to set the restriction threshold at the level of the outgoing flow rate as measured by the outgoing flow sensor 32, and/or as determined from operational parameters of the pump 20 and/or as determined from control input for the pump 20.

Partially clamping the flexible tube to a sufficient extent allows the flow rate in the venous line 12 to be restricted. By gradually opening the clamp, the degree of restriction of the flow rate in the venous line 12 can be reduced until there is no flow rate restriction by the flow-restricting arrangement 28.

In the venous line 12, there is also shown a venous flow sensor 26 that is configured to provide a flow value indicative of the flow rate in the venous line 12. The venous flow sensor 26 may be constituted by an ultrasound flow meter or a mass flow meter.

The venous flow sensor 26 allows a closed loop control to be provided. Due to the closed loop control, it is not necessary to know by how much the tube was squeezed, or which type of equipment was used, in order to maintain the restriction at the set threshold.

For instance, during temporary fluctuations, the controller may issue a control signal to the motorised clamp to squeeze the venous line 12 until the flow rate, as determined by the flow sensor 26, no longer exceeds the restriction threshold.

The controller is configured to receive a venous flow value indicative of the venous flow rate, as determined by the flow sensor 26. The controller comprises decision logic to determine whether or not the venous flow rate exceeds the restriction threshold. If the venous flow value does not exceed the set restriction threshold, the flow-restricting arrangement 26 is not actuated for reasons of venous flow rate fluctuations. If venous flow rate fluctuations lead to the venous flow value exceeding the set restriction threshold, the controller may issue a control signal to the flow-restricting arrangement 28 to adjust (eg increase) the flow restriction until the venous flow rate no longer exceeds the restriction threshold. Likewise, if it is determined that the venous flow value is consistently below the set restriction threshold, the controller may issue a control signal to the flow-restricting arrangement 28 to adjust (eg decrease) the flow restriction until the venous flow rate meets the set restriction threshold.

After the flow-restricting arrangement has been set, the controller continues to monitor the venous flow as determined by the flow sensor 26. If, for any reason, the flow value exceeds the restriction threshold despite a previously appropriate restriction setting, the controller issues a control signal to the flow-restricting arrangement 28 to adjust the restriction threshold.

The controller may also be configured to operate the pump 20 to maintain a pre-determined outgoing flow rate, and to adjust the performance of the pump 20 if the actual outgoing flow rate or differs from the pre-determined outgoing flow rate. The actual outgoing flow rate, or outgoing flow value, may be derived from operational parameters of the pump 20. The outgoing flow value may be determined by the outgoing flow sensor 32.

The pre-determined outgoing flow rate and the restriction threshold may each be set independently, eg, in absolute values, via an input interface.

The controller may be operating in one of various modes, namely a pairing mode, a reservoir level arresting mode, and a venous flow restriction mode. A few of the modes may be operated contemporaneously. The controller comprises a configuration allowing it to set the restriction threshold in the venous line 12 based on the outgoing flow rate through the outlet 24. For the purposes of the present specification, setting the restriction threshold based on the outgoing flow rate is referred to as "pairing mode". The controller also comprises a configuration allowing it to set the outgoing flow rate through the outlet based on the outgoing flow value as determined by the outgoing flow sensor 26. For the purposes of the present specification, setting the outgoing flow rate based on the outgoing flow value is referred to as "reservoir level arresting mode". The controller also comprises a configuration to restrict the venous flow rate and modulate the outgoing flow rate independently of each other. This is referred to herein as "venous flow restriction mode".

The controller also comprises a configuration allowing it to switch between a venous flow restriction mode, the pairing mode, and the reservoir level arresting mode. The controller is configured to activate the pairing mode automatically when a pairing threshold is exceeded. In an embodiment, the pairing threshold is a predetermined outgoing flow rate threshold. The reservoir level arresting mode may be activated automatically when the reservoir level drops below a reservoir safety threshold.

Cardiopulmonary bypass may be initiated with the venous flow restriction mode. The venous restriction threshold may be set manually, eg to 1 lpm. The pairing threshold may be 1 lpm. This may be set manually. The controller may comprise a configuration to set the pairing threshold to the same level as the venous restriction threshold. While the outgoing flow rate is modulated below 1 lpm, the venous restriction threshold remains at 1 lpm. Venous blood is allowed to be drained at up to 1 lpm, although during temporary fluctuations the venous flow rate may be lower.

Other settings of the perfusion system may be set accordingly. For instance, the system may comprise a (air or gas) bubble sensor arrangement to detect bubbles in the circulated blood. If a bubble is detected, this may result in an emergency shut-off of the pump in order to stop the outgoing flow and thereby to stop the bubble from being transported to the patient. During the bypass initiation phase, as priming solution is mixed with blood, the viscosity of the mixture may cause false positives with a fine bubble sensor setting. Thus, when the bypass is initiated by setting the venous restriction from zero flow to an initial flow of 1 lpm, the system may be configured automatically set the bubble threshold may be set to a less sensitive setting (commonly referred to as "coarse" setting). This is because bubble sensors may be "fooled" by the change of viscosity as priming solution is mixing with blood with the result that the pump controller may shut off the main pump by mistake. Once adequate primer/blood mixing has occurred, the system can revert to a "fine" bubble sensing. Other threshold levels, such as a reservoir level safety threshold, may be set accordingly.

In the venous line 12, the actual venous flow rate is monitored by the outgoing flow sensor 26. If, for any reason, the actual venous flow rate exceeds the threshold of 1 lpm, the controller is configured to respond by increasing the flow restriction, until the venous flow rate is at, or below, 1 lpm.

If the pre-determined outgoing flow rate and the restriction threshold are set independently, a change of the pre-determined outgoing flow rate will not affect the restriction threshold.

In practice, the outgoing flow rate may not be increased until after the fluid level in the venous reservoir is sufficiently high.

For instance, the restriction threshold may be set to 1 lpm initially, but it is found that a threshold of 2 lpm may be more appropriate for a particular patient. In that case, the pairing threshold is also set to 2 lpm. The initial level may be based upon the patient size and/or clinician preference.

When the pairing threshold, of eg 1 lpm outgoing flow rate, is exceeded, the system switches to pairing mode. In pairing mode, the venous restriction threshold is set to the outgoing flow rate. This allows the venous restriction threshold to be increased simultaneously with the outgoing flow rate.

Thereby, a clinician can focus on slowly increasing the outgoing flow rate, knowing the venous flow restriction is increased automatically to match the outgoing flow rate.

This facilitates a gentle and safe initiation of bypass by allowing the outgoing (arterial) flow to be increased so as to allow a gentle mixing of solutions, such as crystalloid, and blood into the arterial tree as well as in the venous reservoir until the point at which the target arterial blood flow and crystalloid/blood mixing is sufficient.

Venous flow is started at a low enough rate to permit a clinician to gradually mix in priming solutions (eg, solutions with anticoagulants) into a patient's aorta, while the heart is still pumping more blood than is extracorporeally supplied, to avoid delivering a bolus of prime fluid instead of blood. A sufficient degree of mixing is usually achieved after about 30-60 seconds.

Contemporaneously, the reservoir level sensor arrangement (not shown) may be configured to monitor the blood level in the reservoir 10. If for any reason the blood level in the reservoir 10 is below a low blood level threshold, the system switches to reservoir level arresting mode. The pump 20 is modulated to ensure the outgoing flow rate through the outlet 24 does not exceed the actual venous flow rate as measured by the outgoing flow sensor 26. The reservoir level arresting mode is deactivated when the blood level exceeds the low blood level threshold.

After bypass is initiated, the venous clamp may be modulated to wide open with the main pump delivering required the required outgoing flow rate. Other settings may be changed at this stage. For instance, the bubble sensor threshold may be set to a more sensitive ("fine") setting. The reservoir level safety threshold may be set to a higher level, providing a greater safety margin suitable for a blood circulation rate in the region of 5 lpm while the reservoir is not the primary focus of attention. The pairing mode may be deactivated. To this end, the control system may be set not to automatically reactivate the pairing mode for the remainder of the cardiopulmonary bypass procedure.

Figure 2:
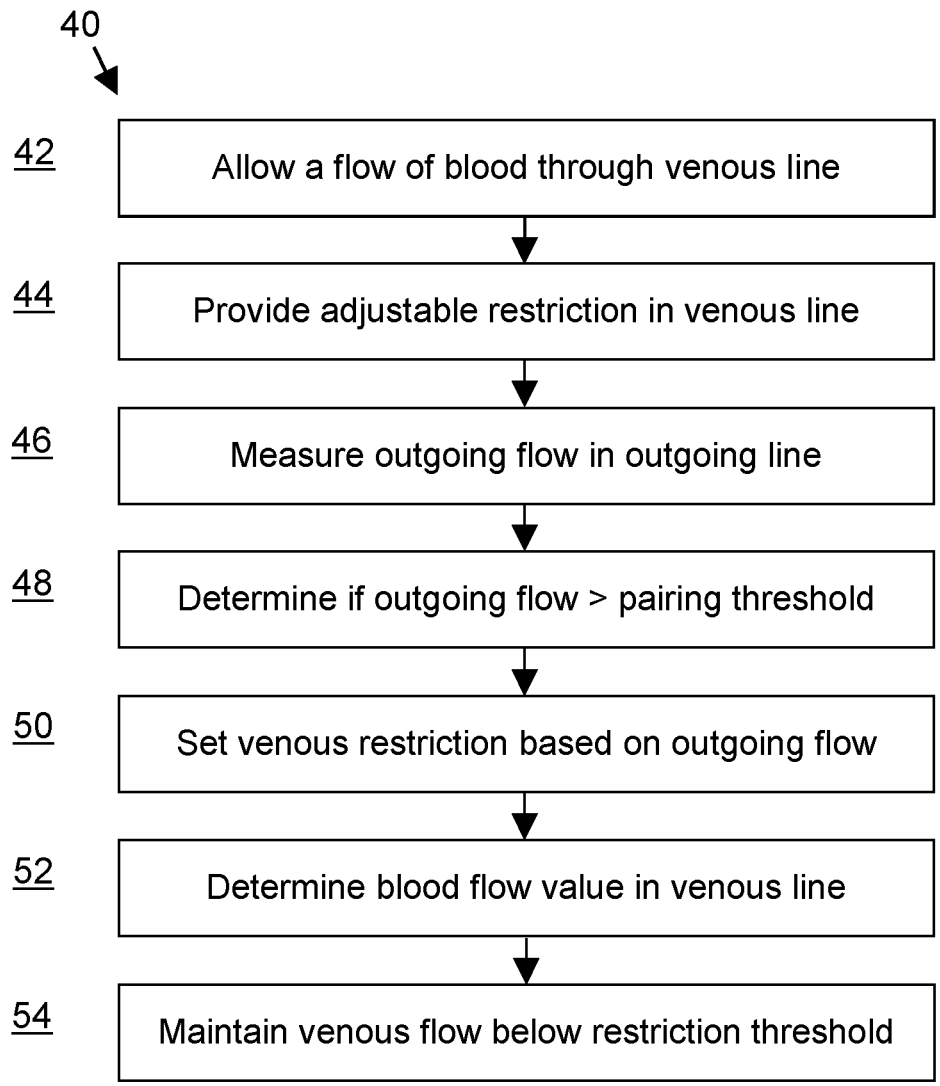
FIG. 2 shows steps of an exemplary sequence of method steps of a method for restricting the flow rate in a blood line accordance with embodiments of the present invention.

In FIG. 2, steps of a control method 40 for restricting the flow rate in a venous line based on the outgoing flow rate (eg the arterial flow rate), are shown. In step 42, blood is permitted to flow through a venous line. In step 44, an adjustable restriction is provided to allow the flow through the blood line to be prevented from exceeding a restriction threshold. In step 46, a flow sensing arrangement is provided in the outgoing line, to provide an outgoing blood flow value indicative of the outgoing flow rate in the outgoing line. The flow sensing arrangement may use a flow sensor to measure actual flow. The flow sensing arrangement may derive the flow rate from pump parameters. The flow sensing arrangement may derive the flow rate from control inputs for the pump. In step 48, a determination is made whether or not the outgoing flow rate as measured by the flow sensing arrangement exceeds a pairing threshold. If the outgoing flow rate exceeds the pairing threshold, then in step 50 a venous restriction threshold is set based on the outgoing flow rate. The venous restriction threshold may be the same level as the outgoing flow rate. The restriction threshold may be regarded as a maximum blood flow rate level. In optional step 52, the venous blood flow value is determined by an optional venous blood flow sensor. In step 54, the venous blood flow is reduced, using the adjustable restriction, to below the restriction threshold. The restriction threshold remains responsive to the flow rate. Ie, if the outgoing flow rate increases, the restriction threshold is automatically increased to match the outgoing flow rate. In embodiments including optional step 52 with a venous flow sensor and closed loop control, if there is a temporary fluctuation causing the venous flow rate to exceed the restriction threshold, the adjustable restriction automatically re-adjusts to limit the flow rate to the restriction threshold.

Threshold values described herein, such as the restriction threshold, the outgoing flow rate, and pressure thresholds, may include a margin to avoid an overshooting response.

By carefully and safely controlling the bypass initiation phase, the risk of a variety of undesirable physiological responses occurring can be reduced. Such responses include a fall in so-called systemic vascular resistance (SVR) due to: dilution of catecholamines in circulation, a sudden decrease in viscosity, temporary hypoxemia due to a severe drop in oxygen content, low pH and low Calcium and Magnesium levels of the priming fluid, and a sudden loss of pulsatile flow. Avoiding SVR provides greater homeostasis which reduces and potentially avoids the activation of stress responses.

The invention claimed is:

1. A control system to restrict the flow rate of blood in a venous line of a perfusion system, wherein the perfusion system comprises a reservoir that is supplied by the venous line and that supplies an outgoing line, wherein the control system comprises:
an outgoing flow sensor configured to determine an outgoing flow value indicative of the outgoing flow rate in the outgoing line,
a controller configured to process the outgoing flow value, and
an adjustable restriction for restricting the flow rate in the venous line to maintain a venous flow rate that does not exceed a venous restriction threshold,
wherein the adjustable restriction is responsive to the controller and wherein the controller comprises a configuration allowing the controller to set the adjustable restriction at the level of the outgoing flow rate, to change the venous restriction threshold in response to a change of the outgoing flow rate, and
wherein the controller is configured to determine if the outgoing flow value exceeds a pre-set pairing threshold and to set, if the outgoing flow value is above the pre-set pairing threshold, the adjustable restriction at the level of the outgoing flow rate.

2. The control system in accordance with claim 1, further comprising a venous flow sensor configured to determine a venous flow value indicative of the venous flow rate in the venous line,
wherein the controller is configured to process the venous flow value, and wherein the adjustable restriction is responsive to the controller to reduce the venous flow rate in the venous line to maintain a venous flow rate that does not exceed the venous restriction threshold.

3. The control system in accordance with claim 1, wherein the controller is configured to set the venous restriction threshold independently of the outgoing flow rate if the outgoing flow rate is below the pairing threshold.

4. The control system in accordance with claim 1, wherein one or more of the flow sensors are constituted by an arrangement determining the flow rate from pump parameters of one or more pumps of the perfusion system, and/or by an arrangement determining the flow rate from control input for the one or more pumps.

5. The control system in accordance with claim 1, further comprising a reservoir level sensor to determine a reservoir level of fluid in the reservoir, wherein the controller is configured to modulate the outgoing flow rate to prevent the outgoing flow rate from exceeding the venous flow rate if the reservoir level is below a reservoir level safety threshold, so as to arrest a decrease of fluid in the reservoir.

6. The control system in accordance with claim 1, wherein the system comprises a reservoir level sensor to determine a reservoir level of fluid in the reservoir, and wherein the controller is configured to maintain a venous flow rate that does not exceed the level of the outgoing flow rate if the reservoir level is above a reservoir level safety threshold.

7. The control system in accordance with claim 1, further configured to alter a threshold level or sensitivity as monitored by one or more sensors of the perfusion system in response to a change of the venous restriction threshold and/or of the outgoing flow value.

8. The control system in accordance with claim 7, configured to alter the threshold level or sensitivity synchronously with a change of the venous restriction threshold and/or the outgoing flow value.

9. The control system in accordance with claim 7, configured to alter the threshold level or sensitivity if the venous restriction threshold and/or the outgoing flow value exceeds or falls below a sensitivity threshold.

10. The control system in accordance with claim 7, wherein the threshold level or sensitivity as monitored by one or more sensors is for one or more of a reservoir level safety threshold, a bubble value, a pressure threshold, a flow rate threshold, a blood value, or combinations thereof.

11. The control system in accordance with claim 1, wherein the controller comprises a processor and software instructions implemented by the processor, and wherein the adjustable restriction comprises instructions implemented by the processor.

12. A method of restricting the flow rate of blood in a venous line of a perfusion system, wherein the perfusion system comprises a reservoir that is supplied by the venous line and that supplies an outgoing line, a controller, and an adjustable restriction responsive to the controller for restricting the flow rate in the venous line to maintain a venous flow rate that does not exceed a venous restriction threshold, the method comprising:
   determining an outgoing flow value indicative of the outgoing flow rate in the outgoing line,
   the controller processing the outgoing flow value and setting the adjustable restriction at the level of the outgoing flow rate,
   changing the venous restriction threshold in response to a change of the outgoing flow rate, and
   determining if the outgoing flow value exceeds a pre-set pairing threshold and, if the outgoing flow value is above the pre-set pairing threshold, setting the adjustable restriction at the level of the outgoing flow rate.

13. The method in accordance with claim 12, wherein the perfusion system further comprises a venous flow sensor configured to determine a venous flow value indicative of the venous flow rate in the venous line, the method further comprising:
   the controller processing the venous flow value, and adjusting the adjustable restriction to reduce the venous flow rate in the venous line to maintain a venous flow rate that does not exceed the venous restriction threshold.

14. The method in accordance with claim 12, further comprising setting the venous restriction threshold independently of the outgoing flow rate if the outgoing flow rate is below the pairing threshold.

15. The method in accordance with claim 12, wherein the venous flow rate and/or the outgoing flow rate is determined from pump parameters of one or more pumps of the perfusion system, and/or by an arrangement determining the flow rate from control input for the one or more pumps.

16. The method in accordance with claim 12, wherein the perfusion system further comprises a reservoir level sensor to determine a reservoir level of fluid in the reservoir, the controller modulating the outgoing flow rate to prevent the outgoing flow rate from exceeding the venous flow rate if the reservoir level is below a reservoir level safety threshold, so as to arrest a decrease of fluid in the reservoir.

17. The method in accordance with claim 12, wherein the system comprises a reservoir level sensor to determine a reservoir level of fluid in the reservoir, and wherein the controller maintains a venous flow rate that does not exceed the level of the outgoing flow rate if the reservoir level is above a reservoir level safety threshold.

18. The method in accordance with claim 12, further comprising altering a threshold level or sensitivity as monitored by one or more sensors of the perfusion system in response to a change of the venous restriction threshold and/or of the outgoing flow value.

19. The method in accordance with claim 18, comprising altering the threshold level or sensitivity synchronously with a change of the venous restriction threshold and/or the outgoing flow value.

20. The method in accordance with claim 18, comprising altering the threshold level or sensitivity if the venous restriction threshold and/or the outgoing flow value exceeds or falls below a sensitivity threshold.

21. The method in accordance with claim 18, wherein the threshold level or sensitivity as monitored by one or more sensors is for one or more of a reservoir level safety threshold, a bubble value, a pressure threshold, a flow rate threshold, a blood value, or combinations thereof.

* * * * *